(12) United States Patent
Wang et al.

(10) Patent No.: US 12,067,717 B2
(45) Date of Patent: Aug. 20, 2024

(54) MEDICAL IMAGE ANALYZING SYSTEM AND METHOD THEREOF

(71) Applicant: National Taiwan University, Taipei (TW)

(72) Inventors: Wei-Chung Wang, Taipei (TW); Wei-Chih Liao, Taipei (TW); Kao-Lang Liu, Taipei (TW); Po-Ting Chen, Taipei (TW); Po-Chuan Wang, Taipei (TW); Ting-Hui Wu, Taipei (TW)

(73) Assignee: National Taiwan University, Taipei (TW)

( * ) Notice: Subject to any disclaimer, the term of this patent is extended or adjusted under 35 U.S.C. 154(b) by 403 days.

(21) Appl. No.: 17/507,948

(22) Filed: Oct. 22, 2021

(65) Prior Publication Data

US 2022/0130038 A1 Apr. 28, 2022

Related U.S. Application Data

(60) Provisional application No. 63/104,568, filed on Oct. 23, 2020.

(51) Int. Cl.
*G06T 7/00* (2017.01)
*A61B 5/00* (2006.01)
(Continued)

(52) U.S. Cl.
CPC ............ *G06T 7/0012* (2013.01); *A61B 5/425* (2013.01); *A61B 5/4887* (2013.01); *A61B 5/726* (2013.01); *A61B 5/7267* (2013.01); *G06N 3/08* (2013.01); *G06T 7/70* (2017.01); *G06T 7/73* (2017.01); *G06V 10/774* (2022.01); *G06V 10/776* (2022.01); *G06V 10/82* (2022.01); *G16H 30/20* (2018.01); *G06T 2207/20016* (2013.01); *G06T 2207/20064* (2013.01);
(Continued)

(58) Field of Classification Search
CPC .......... G06T 7/00; G06T 7/0012; G06T 7/70; G06T 7/73; G16H 30/20; G06N 3/08; G06V 10/82; G06V 10/774; G06V 10/776; A61B 5/425; A61B 5/726; A61B 5/4887; A61B 5/7267
See application file for complete search history.

(56) References Cited

U.S. PATENT DOCUMENTS 10,803,987 B2 * 10/2020 Bériault ................. G06N 3/045
11,583,698 B2 *  2/2023 Yin ........................ A61N 5/103

* cited by examiner

*Primary Examiner* — Tuan H Nguyen
(74) *Attorney, Agent, or Firm* — Amin, Turocy & Watson, LLP

(57) ABSTRACT

A medical image analyzing system and a medical image analyzing method are provided and include inputting at least one patient image into a first model of a first neural network module to obtain a result having determined positions and ranges of an organ and a tumor of the patient image; inputting the result into a plurality of second models of a second neural network module, respectively, to obtain a plurality of prediction values corresponding to each of the plurality of second models and a model number predicting having cancer in the plurality of prediction values; and outputting a determined result based on the model number predicting having cancer and a number threshold value. Further, processes between the first model and the second models can be automated, thereby improving identification rate of pancreatic cancer.

22 Claims, 2 Drawing Sheets

(51) Int. Cl.
  *G06N 3/08*    (2023.01)
  *G06T 7/70*    (2017.01)
  *G06T 7/73*    (2017.01)
  *G06V 10/774*  (2022.01)
  *G06V 10/776*  (2022.01)
  *G06V 10/82*   (2022.01)
  *G16H 30/20*   (2018.01)
(52) U.S. Cl.
  CPC ............... *G06T 2207/20081* (2013.01); *G06T 2207/20084* (2013.01); *G06T 2207/30096* (2013.01); *G06T 2207/30204* (2013.01); *G06V 2201/031* (2022.01)

MEDICAL IMAGE ANALYZING SYSTEM AND METHOD THEREOF

BACKGROUND

1. Technical Field

The present disclosure relates to image analyzing system and method, and more particularly, to medical image analyzing system and method.

2. Description of Related Art

In the current medical practice, pancreatic cancer is one of the cancers that are difficult to detect early, and the survival rate of pancreatic cancer decreases significantly once the tumor size exceeds 2 cm. In the prior art, computerized tomography (CT) imaging is currently the main method for detecting and evaluating pancreatic cancer, but the detection efficiency still depends on the personal experience of radiologists. For example, when the tumor size is less than 2 cm, about 40% of the tumor cannot be detected, which reflects the fact that manual review and diagnosis are too subjective, and it is easy to misdiagnose due to human factors.

Therefore, there is a need in the art to propose a medical image analyzing system and a medical image analyzing method for identifying pancreatic cancer and improving the identification rate of pancreatic cancer.

SUMMARY

In view of the aforementioned problems of the prior art, the present disclosure provides a medical image analyzing system, which comprises a first neural network module having a first model and configured to input at least one patient image into the first model to obtain a result having determined positions and ranges of an organ and a tumor of the patient image; a second neural network module having a plurality of second models and configured to respectively input the result having the determined positions and ranges of the organ and the tumor of the patient image into the plurality of second models to obtain a plurality of prediction values corresponding to each of the plurality of second models and a model number predicting having cancer in the plurality of prediction values; and a determining module configured to output a determined result based on the model number predicting having cancer and a number threshold value.

In the aforementioned medical image analyzing system, the present disclosure further comprises a database stored with a plurality of images, organ position and range markers and tumor position and range markers, wherein the plurality of images, the organ position and range markers and the tumor position and range markers are interlinked to use as a first training set.

In the aforementioned medical image analyzing system, the first neural network module is trained to obtain the first model based on the first training set, wherein the first neural network module is a model searched by using a coarse-to-fine neural structure search (C2FNAS), and wherein the first neural network module uses an Adam optimizer and a cosine annealing learning rate scheduler to adjust a learning rate in a range of $10^{-4}$ to $10^{-5}$, and a loss function is set to a Dice loss combined with a categorical cross-entropy loss.

In the aforementioned medical image analyzing system, the first neural network module obtains a result having determined positions and ranges of an organ and a tumor of the plurality of images by inputting the plurality of images into the first model and uses the result as a second training set.

In the aforementioned medical image analyzing system, the second neural network module is trained to obtain the plurality of second models based on the second training set, wherein the second neural network module is a DenseNet-121, and wherein the second neural network module uses an Adam optimizer and a cosine annealing learning rate scheduler to adjust a learning rate in a range of $10^{-4}$ to $10^{-5}$, and a loss function is set to a binary classification loss.

In the aforementioned medical image analyzing system, the second neural network module evenly divides the plurality of images and the second training set into a plurality of folds, and repeatedly uses one of the plurality of folds as a validation set and the others of the plurality of folds as a training set in a non-repetitive manner to train and obtain the plurality of second models.

In the aforementioned medical image analyzing system, the present disclosure further comprises a threshold-value selection module configured to plot a plurality of curves for the plurality of prediction values, wherein a plurality of threshold values for determining whether there is cancer are determined from each of the plurality of curves, such that the second neural network module determines whether the plurality of prediction values predict having cancer based on the plurality of threshold values.

In the aforementioned medical image analyzing system, the plurality of curves are receiver operating characteristic curves, and the plurality of threshold values are corresponding threshold values corresponding to maximum values of a plurality of Youden indexes or a combination of a sensitivity and a specificity.

In the aforementioned medical image analyzing system, the plurality of Youden indexes are calculated from the sensitivity and the specificity corresponding to each point in each of the plurality of curves according to a formula Youden index=Sensitivity+Specificity−1, wherein the combination of the sensitivity and the specificity are calculated from the sensitivity and the specificity corresponding to the each point in each of the plurality of curves according to a formula Combination of Sensitivity and Specificity= Sensitivity×N+Specificity, and wherein the N is any number.

In the aforementioned medical image analyzing system, the determining module respectively calculates corresponding positive likelihood ratios for performance of different model numbers predicting having cancer in the plurality of second models to determine the number threshold value, and wherein the determining module outputs the determined result of having cancer when the model number predicting having cancer is greater than or equal to the number threshold value.

In the aforementioned medical image analyzing system, the determining module selects a least number in the different model numbers predicting having cancer corresponding to the positive likelihood ratio greater than 1 as the number threshold value.

In the aforementioned medical image analyzing system, the present disclosure further comprises an image preprocessing module configured to process the patient image by resampling, windowing and normalization before inputting the first model or the plurality of second models.

The present disclosure further provides a medical image analyzing method, which comprises the steps of: obtaining at least one patient image; inputting the patient image into a first model of a first neural network module to obtain a result having determined positions and ranges of an organ and a tumor of the patient image; inputting the result having the determined positions and ranges of the organ and the tumor of the patient image into the plurality of second models of a second neural network module, respectively, to obtain a plurality of prediction values corresponding to each of the plurality of second models and a model number predicting having cancer in the plurality of prediction values; and outputting a determined result by a determining module according to the model number predicting having cancer and a number threshold value.

In the aforementioned medical image analyzing method, the present disclosure further comprises the step of: interlinking a plurality of images, organ position and range markers and tumor position and range markers to use as a first training set via a database stored with the plurality of images, the organ position and range markers and the tumor position and range markers.

In the aforementioned medical image analyzing method, the first neural network module is trained to obtain the first model based on the first training set, wherein the first neural network module is a model searched by using a coarse-to-fine neural structure search (C2FNAS), and wherein the first neural network module uses an Adam optimizer and a cosine annealing learning rate scheduler to adjust a learning rate in a range of $10^{-4}$ to $10^{-5}$, and a loss function is set to a Dice loss combined with a categorical cross-entropy loss.

In the aforementioned medical image analyzing method, the first neural network module obtains a result having determined positions and ranges of an organ and a tumor of the plurality of images by inputting the plurality of images into the first model and uses the result as a second training set.

In the aforementioned medical image analyzing method, the second neural network module is trained to obtain the plurality of second models based on the second training set, wherein the second neural network module is a DenseNet-121, and wherein the second neural network module uses an Adam optimizer and a cosine annealing learning rate scheduler to adjust a learning rate in a range of $10^{-4}$ to $10^{-5}$, and a loss function is set to a binary classification loss.

In the aforementioned medical image analyzing method, the second neural network module evenly divides the plurality of images and the second training set into a plurality of folds, and repeatedly uses one of the plurality of folds as a validation set and the others of the plurality of folds as a training set in a non-repetitive manner to train and obtain the plurality of second models.

In the aforementioned medical image analyzing method, the present disclosure further comprises the step of: plotting a plurality of curves for the plurality of prediction values by a threshold-value selection module, wherein a plurality of threshold values for determining whether there is cancer are determined from each of the plurality of curves, such that the second neural network module determines whether the plurality of prediction values predict having cancer based on the plurality of threshold values.

In the aforementioned medical image analyzing method, the plurality of curves are receiver operating characteristic curves, and the plurality of threshold values are corresponding threshold values corresponding to maximum values of a plurality of Youden indexes or a combination of a sensitivity and a specificity.

In the aforementioned medical image analyzing method, the plurality of Youden indexes are calculated from the sensitivity and the specificity corresponding to each point in each of the plurality of curves according to a formula Youden index=Sensitivity+Specificity−1, wherein the combination of the sensitivity and the specificity are calculated from the sensitivity and the specificity corresponding to the each point in each of the plurality of curves according to a formula Combination of Sensitivity and Specificity= Sensitivity×N+Specificity, and wherein the N is any number.

In the aforementioned medical image analyzing method, the determining module respectively calculates corresponding positive likelihood ratios for performance of different model numbers predicting having cancer in the plurality of second models to determine the number threshold value, and wherein the determining module outputs the determined result of having cancer when the model number predicting having cancer is greater than or equal to the number threshold value.

In the aforementioned medical image analyzing method, the determining module selects a least number in the different model numbers predicting having cancer corresponding to the positive likelihood ratio greater than 1 as the number threshold value.

In the aforementioned medical image analyzing method, the present disclosure further comprises the step of: enabling an image preprocessing module to process the patient image by resampling, windowing and normalization before inputting the first model or the plurality of the second models.

In summary, the medical image analyzing system and method according to the present disclosure have higher sensitivity than radiologists in identifying pancreatic cancer, which means that the medical image analyzing system and method according to the present disclosure can effectively assist radiologists in reducing their clinical missed diagnosis rate, especially in the case of tumors less than 2 cm in size. Therefore, the situation that about 40% of the tumors cannot be detected when the tumor is less than 2 cm in size can be effectively improved. In addition, the medical image analyzing system and method according to the present disclosure are automated processes. After directly inputting the original medical image, the medical image analyzing system and method according to the present disclosure can automatically identify the potential positions and ranges of pancreas and tumor and automatically classify whether the original medical image contains pancreatic cancer.

DETAILED DESCRIPTION OF THE EMBODIMENTS

The following illustrative embodiments are provided to illustrate the present disclosure, these and other advantages and effects can be apparent to those in the art after reading this specification.

Figure 1:
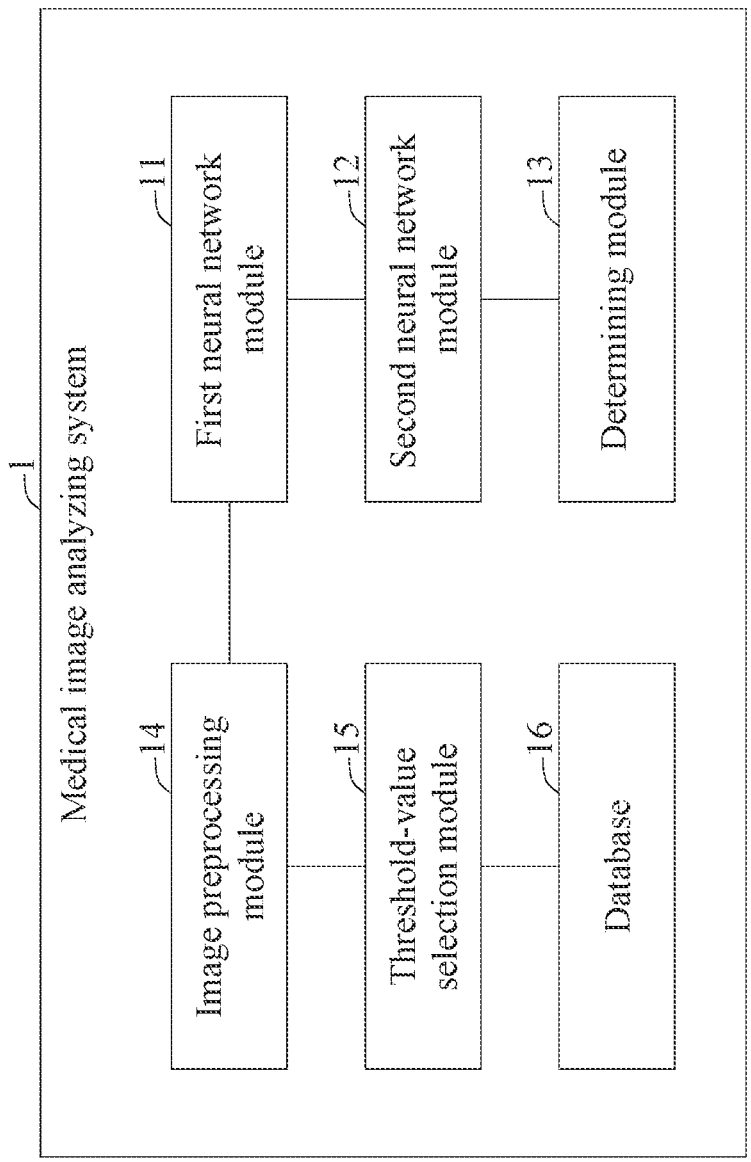
FIG. 1 is a system architecture diagram of a medical image analyzing system according to the present disclosure.

Referring to FIG. 1, a medical image analyzing system 1 according to the present disclosure includes a first neural network module 11, a second neural network module 12, a determining module 13, an image preprocessing module 14, a threshold-value selection module 15 and a database 16. The medical image analyzing system 1 according to the present disclosure can operate on devices such as mobile phones, tablet computers, laptops, desktop computers, servers, or cloud servers. The first neural network module 11, the second neural network module 12, the determining module 13, the image preprocessing module 14 and the threshold-value selection module 15 can respectively be code fragments, software, or firmware stored in the database 16 or a storage unit, and can be executed by a processing unit, and can also be implemented by other hardware or combinations of software and hardware. The processing unit can be a central processing unit (CPU), a microprocessor, a graphics processing unit (GPU), or an application specific integrated circuit (ASIC). The storage unit can be a combination of any type of fixed or removable random-access memory (RAM), read-only memory (ROM), flash memory, hard disk, soft disk, database, or similar elements. However, the present disclosure is not limited thereto.

In an embodiment, the first neural network module 11 has a first model. After inputting at least one patient image into the first model, a result having determined positions and ranges of an organ and a tumor of the patient image can be obtained. The second neural network module 12 has a plurality of second models. After inputting the result having determined positions and ranges of the organ and the tumor of the patient image into the plurality of second models, respectively, a plurality of prediction values corresponding to each of the plurality of second models and a model number predicting having cancer in the plurality of prediction values can be obtained. In an embodiment, the patient image can be a two-dimensional (2D) CT image or a three-dimensional (3D) CT image, and the present disclosure is not limited as such. Both the first model and the second models are models trained by a neural network. The training stages of the first model and the second models are described below.

The database 16 can store a plurality of images, organ position and range markers, and tumor position and range markers, and the plurality of images, organ position and range markers, and tumor position and range markers are interlinked (e.g., linked to each other). The interlink referred herein is to plot the organ position and range markers, the tumor position and range markers, or both on the image at the same time, and the organ can be a pancreas. In addition, the image can be a 2D CT image or a 3D CT image, the organ position and range markers can be a contour of the pancreas, the tumor position and range markers can be a contour of the tumor portion in the pancreas, and the organ position and range markers and the tumor position and range markers can be marked by an experienced radiologist according to actual diagnosis data. In an embodiment, all data of the plurality of interlinked images, organ position and range markers and tumor position and range markers are used as a first training set.

The first neural network module 11 can train and obtain the first model based on the first training set. The first neural network module 11 is a deep learning model architecture based on SegNet or U-Net, for instance, a model searched by NVIDIA using a coarse-to-fine neural structure search (C2FNAS). During a training process, the first neural network module 11 can use Adam optimizer and cosine annealing learning rate scheduler to adjust a learning rate in a range of $10^{-4}$ to $10^{-5}$, a loss function is set to a Dice loss combined with a categorical cross-entropy loss, and a batch size is 8.

In an embodiment, the deep learning model architecture based on SegNet or U-Net can be as follows. In a first level, an image of 96×96×96 pixels is inputted; after feature extraction is performed by a stem 3×3×3 convolution layer, 32 feature images of 96×96×96 pixels are outputted; after feature extraction using the stem 3×3×3 convolution layer with a stride of 2, 64 feature images of 48×48×48 pixels are outputted; and then entering to a second level. In the second level, another 64 feature images of 48×48×48 pixels are obtained via a 2D 3×3×1 convolution layer with said 64 feature images of 48×48×48 pixels (feature 2-1); after using pseudo 3D (P3D) 3×3×1+1×1×3 convolution layers, the feature images are added with the feature 2-1 to obtain another 64 feature images of 48×48×48 pixels (feature 2-2); after feature extraction using a 3D 3×3×3 convolution layer with a stride of 2, 128 feature images of 24×24×24 pixels are outputted; and then entering to a third level. In the third level, after feature extraction using the 3D 3×3×3 convolution layer with said 128 feature images of 24×24×24 pixels, another 128 feature images of 24×24×24 pixels (feature 3-1) are obtained; after feature extraction using the 3D 3×3×3 convolution layer with a stride of 2, 256 feature images of 12×12×12 pixels are outputted; and then entering to a fourth level. In the fourth level, after feature extraction using the 2D 3×3×1 convolution layer with a stride of 2 with said 256 feature images of 12×12×12 pixels (feature 4-1), 512 feature images of 6×6×6 pixels are outputted; and then a process of feature decoding can be performed.

After the 512 images of 6×6×6 pixels are feature restored by trilinear upsample and added with another 256 feature images of 12×12×12 pixels (which are obtained after the feature 4-1 passes through the 3D 3×3×3 convolution layer), 256 feature images of 12×12×12 pixels are outputted. Said 256 feature images of 12×12×12 pixels pass through the 3D 3×3×3 convolution layer to generate another 256 feature images of 12×12×12 pixels. After said another 256 feature images of 12×12×12 pixels are feature restored by trilinear upsample and added with another 128 feature images of 24×24×24 pixels (which are obtained after the feature 3-1 passes through the P3D 3×3×1+1×1×3 convolution layers), 128 feature images of 24×24×24 pixels are outputted. After said 128 feature images of 24×24×24 pixels are feature restored by trilinear upsample and added with another 64 feature images of 48×48×48 pixels (which are obtained after the feature 2-2 passes through the 3D 3×3×3 convolution layer), 64 feature images of 48×48×48 pixels are outputted. Said 64 feature images of 48×48×48 pixels (feature 5-1) pass through the 2D 3×3×1 convolution layer and another 64 feature images of 48×48×48 pixels (feature 5-2) are obtained. After said another 64 feature images of 48×48×48 pixels pass through the 3D 3×3×3 convolution layer and add with the feature 5-1, another 64 feature images of 48×48×48 pixels are obtained. After said another 64 feature images of 48×48×48 pixels pass through the stem 3×3×3 convolution layer, another 64 feature images of 48×48×48 pixels are obtained. After said another 64 feature images of 48×48×48 pixels and the feature 5-2 are feature restored by trilinear upsample and added together, 32 feature images of 96×96×96 pixels are outputted. Finally, after performing feature decode to said 32 feature images of 96×96×96 pixels via the stem 3×3×3 convolution layer, one feature image of 96×96×96 pixels is outputted. At this time, the size of the feature image of the last level is equal to the size of the image of the first level.

The first neural network module 11 can input the plurality of images to the trained first model so as to obtain a result of determined positions and ranges of an organ and a tumor of the plurality of images and use the result as a second training set. The result can be a mask of the positions and ranges of the organ and the tumor, or the result can be an image of the positions and ranges of the organ and the tumor that have been marked, and the present disclosure is not limited as such. The second neural network module 12 can train and obtain the second models based on the second training set. The second neural network module 12 is a deep learning model architecture of DenseNet-121. During a training process, the second neural network module 12 can use Adam optimizer and cosine annealing learning rate scheduler to adjust a learning rate in a range of $10^{-4}$ to $10^{-5}$, a loss function is set to a binary classification loss, and a batch size is 16. In an embodiment, the second neural network module 12 can first evenly divide the plurality of images and the second training set (take the result is a mask of the positions and ranges of the organ and the tumor as an example) into a plurality of folds (subsets), and repeatedly use one of the plurality of folds as a validation set and the others as a training set in a non-repetitive manner so as to train and obtain the plurality of second models. For example, the second neural network module 12 can first evenly divide the plurality of images and the second training set into five folds numbered 1 to 5, and train number 1 (using as a validation set) and numbers 2-5 (using as a training set) to obtain a first second model. The second neural network module 12 can train number 2 (using as a validation set) and numbers 1, 3-5 (using as a training set) to obtain a second model. The second neural network module 12 can train number 3 (using as a validation set) and numbers 1, 2, 4, 5 (using as a training set) to obtain a third second model. The second neural network module 12 can train number 4 (using as a validation set) and numbers 1-3, 5 (using as a training set) to obtain a fourth second model. The second neural network module 12 can train number 5 (using as a validation set) and numbers 1-4 (using as a training set) to obtain a fifth second model. That is, the number of the folds is equal to the number of the second models trained. The trained second models can output a prediction value corresponding to an input image, and the prediction value can be used for classification (predicting having cancer or not having cancer).

In an embodiment, a deep learning model architecture of DenseNet-121 can be as follows: input an image to a 7×7 convolutional layer with a stride of 2; connect to a 3×3 maximum pooling layer with a stride of 2; sequentially pass through a plurality of dense blocks (e.g., four dense blocks) and a plurality of transition blocks (e.g., three transition blocks); sequentially enter 7×7 global average pooling layer, dense layer and softmax layer; and finally output a prediction value.

The above described the training stages of the first model and the second models. In actual application stage, a program can be written to directly use the output of the first model as the input of the second models so as to achieve automation effect. For example, python (version 3.6.8) can be used to write code. The first model and the second models can be implemented using Tensorflow software library or NVIDIA Clara Train SDK framework (version 3.0). Therefore, a user only needs to input one or a plurality of patient images to the first model, and the first model will output a result having determined positions and ranges of an organ and a tumor of the patient image. Said result can be automatically inputted to the plurality of second models so as to output a prediction value corresponding to the patient image. In the case of one patient image and a plurality of second models, different prediction values of one patient image in different second models will be obtained. In the case of a plurality of patient images and a plurality of second models, a plurality of different prediction values of each of the plurality of patient images in different second models will be obtained.

Whether in the training stage or the application stage, the following method can be used to classify the prediction value. The threshold-value selection module 15 can determine a threshold value to classify the prediction value as predicting having cancer or not having cancer. For instance, after obtaining the plurality of prediction values, the threshold-value selection module 15 uses a specific threshold value to determine the plurality of prediction values so as to calculate statistical indicators (which include sensitivity and specificity, etc.) corresponding to the specific threshold value. Further, a plurality of sensitivities and specificities calculated according to possible values of the plurality of specific threshold values can be plotted as a curve, and the curve can be a receiver operating characteristic (ROC) curve. Then, from the receiver operating characteristic curve, statistical indicators such as area under receiver operating characteristic (AUC) curve, a plurality of Youden indexes, or a combination of sensitivity and specificity, etc. can be obtained. The plurality of Youden indexes are calculated from the sensitivity and the specificity corresponding to each point in the curve according to the formula: Youden index=Sensitivity+Specificity−1. The combination of sensitivity and specificity is calculated from the sensitivity and the specificity corresponding to each point in the curve according to the formula: Combination of Sensitivity and Specificity=Sensitivity×N+Specificity, where N is any number (e.g., 1 or 2, or even a number less than 1). In the present disclosure, the threshold values corresponding to the maximum values in the plurality of Youden indexes are used as threshold values, or the threshold values corresponding to the maximum values of the combination of sensitivity and specificity are used as threshold values, and the present disclosure is not limited as such. When the prediction value of the image (or patient image) is greater than the threshold value, the prediction value can be classified as predicting having cancer (positive), otherwise it can be classified as predicting not having cancer (negative).

In an embodiment, taking the aforementioned five second models as examples, one or a plurality of images (or patient images) are respectively inputted into five second models to obtain five sets of predictions values corresponding to the five second models, respectively. Each set of prediction values can include a prediction value or a plurality of prediction values according to the difference of the number of images inputted. In the case of inputting a plurality of images of a patient into a second model to obtain a plurality of prediction values, another prediction value representing whether having cancer can be defined by a ratio of the number of images classified as predicting having cancer in the plurality of images to the total number of the plurality of images. If a plurality of prediction values are obtained by inputting a plurality of images corresponding to each of the plurality of patients, whether the plurality of prediction values are predicting having cancer or not can be determined by the aforementioned process of curve plotting and the aforementioned process of determining the threshold value representing having cancer or not. Since the five second models may have different results for the same set of images, for example, a few of the five second models may determine having cancer, the determining module 13 is configured to decide how many second models determining having cancer are needed before outputting the total result as having cancer.

The determining module 13 first respectively calculates positive likelihood ratio for the performance of different model numbers predicting having cancer in the plurality of second models so as to decide and determine whether the final result is a number threshold value (e.g., quantity threshold value) of the plurality of second models representing positive (i.e., predicting having cancer). The formula of positive likelihood ratio is: "the proportion of X models predicting positive in the ground truth positive image" divided by "the proportion of X models predicting positive in the ground truth negative image," where each different X corresponds to a positive likelihood ratio. As shown in Table 1, taking five second models as an example, when zero (X=0) or one (X=1) or two (X=2) models predicting positive are considered, the positive likelihood ratio is 0; when three models predicting positive (X=3) are considered, the positive likelihood ratio is 0.93; and when four models predicting positive (X=4) are considered, the positive likelihood ratio is 4.25. The determining module 13 selects the least number (e.g., least quantity) in the different model numbers predicting having cancer corresponding to a positive likelihood ratio greater than 1 as the number threshold value. In an embodiment, the number threshold value is four second models; as such, in five second models, when four or more than four prediction values corresponding to the second models predict having cancer, the determined result outputted by the determining module 13 is having cancer. When only three second models in the five second models determine having cancer, the determined result outputted by the determining module 13 is not having cancer.

TABLE 1

| The number of models predicting positive in second models | The number of cancer patients predicted (n = 437) | The control number predicted (n = 586) | Positive likelihood ratio |
| --- | --- | --- | --- |
| 5 | 409 | 0 | Inf (=(409/437)/(0/586)) |
| 4 | 19 | 6 | 4.25 (=(19/437)/(6/586)) |
| 3 | 9 | 13 | 0.93 (=(9/437)/(6/586)) |
| 2 | 0 | 14 | 0 (=(0/437)/(14/586)) |
| 1 | 0 | 75 | 0 (=(0/437)/(75/586)) |
| 0 | 0 | 478 | 0 (=(0/437)/(478/586)) |

In an embodiment, whether in the training stage or in the application stage, the image preprocessing module 14 can be used to process the patient image or the image in the database 16 before inputting the first model or the second models. For example, before inputting the first model, the image can be resampled to the same spacing (1 mm, 1 mm, 1 mm) by using a linear interpolation and a nearest-neighbor interpolation, and then the window width and the window level of the image are set to 450 HU and 25 HU (Hounsfield unit), respectively. Finally, the image is normalized, that is, the pixel intensity value of the image is set between 0 and 1. For another example, before inputting the second models, a portion without the organ position and range markers and the tumor position and range markers in the image can first be removed, and then fragments less than 1000 voxels (about 200 mm$^3$) are removed so as to prevent the second models from generating deviations. Next, the image can be resampled to the same spacing (1 mm, 1 mm, 5 mm) by using a linear interpolation and a nearest-neighbor interpolation, and then the window width and the window level of the image are set to 250 HU and 75 HU, respectively. Finally, the image is normalized, that is, the pixel intensity value of the image is set between 0 and 1.

Figure 2:
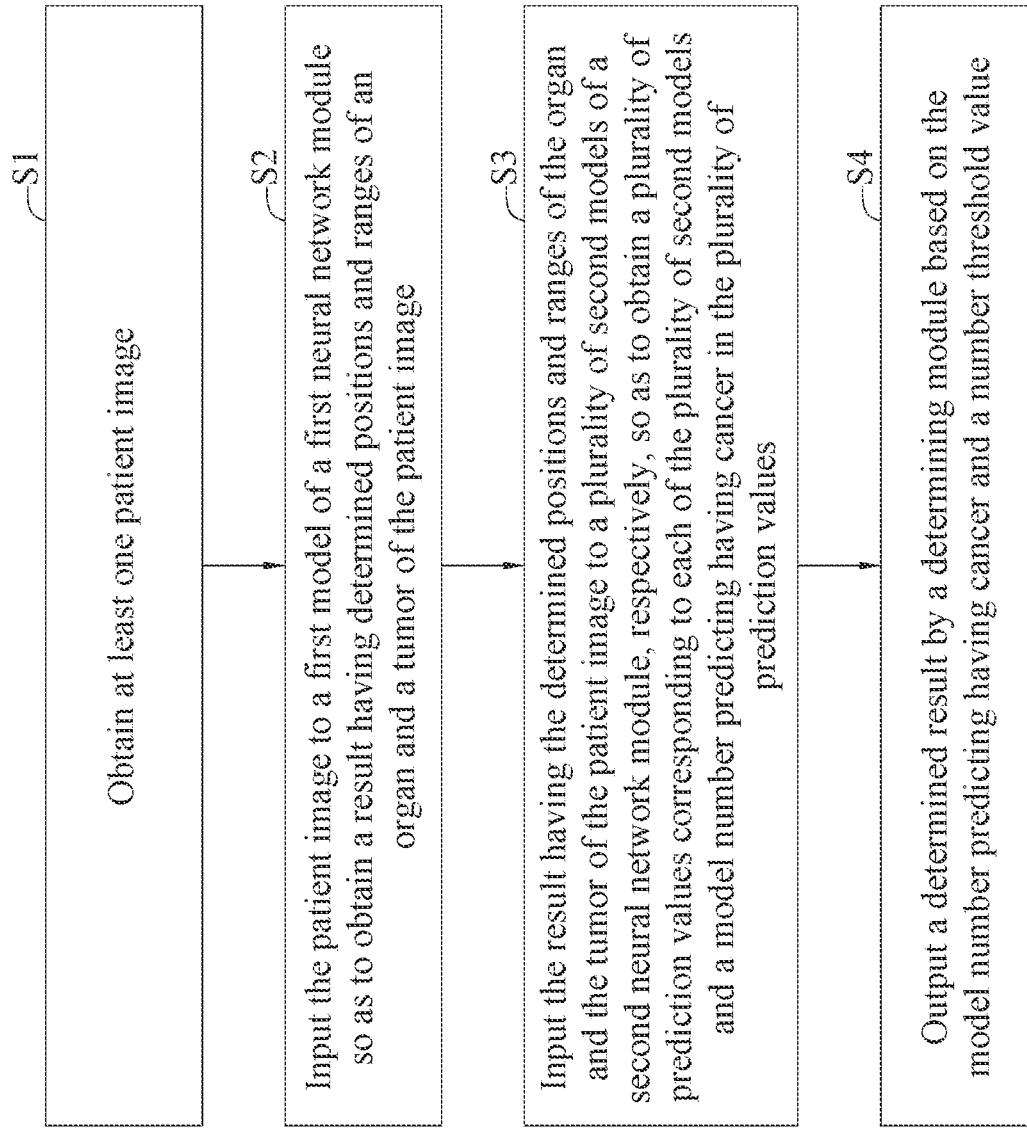
FIG. 2 is a flowchart illustrating a medical image analyzing method according to the present disclosure.

Referring to FIG. 2, a medical image analyzing method according to the present disclosure is further provided. The medical image analyzing method according to the present disclosure can be used in the medical image analyzing system 1. The same technical content between the medical image analyzing method according to the present disclosure and the medical image analyzing system will not be repeated herein.

In step S1, at least one patient image is obtained first. In step S2, the patient image is inputted to a first model of a first neural network module 11 so as to obtain a result having determined positions and ranges of an organ and a tumor of the patient image. In step S3, the result having the determined positions and ranges of the organ and the tumor of the patient image is respectively inputted to a plurality of second models of a second neural network module 12 so as to obtain a plurality of prediction values corresponding to each of the plurality of second models and a model number predicting having cancer in the plurality of prediction values. In step S4, a determining module 13 outputs a determined result based on the model number predicting having cancer and a number threshold value. The training methods of the first model and the second models are the same as the training methods of the first model and the second models in the medical image analyzing system and will not be repeated herein.

In an embodiment, step S3 further includes the following steps: the threshold-value selection module 15 plots a plurality of curves for the plurality of prediction values, so a plurality of threshold values for determining whether there is cancer can be determined from each of the plurality of curves, so that the second neural network module 12 can determine whether the plurality of prediction values predict having cancer based on the plurality of threshold values.

In an embodiment, in step S4, the determining module 13 respectively calculates the corresponding positive likelihood ratio for the performance of different model numbers predicting having cancer in the plurality of second models so as to determine the number threshold value; and when the model number predicting having cancer is greater than or equal to the number threshold value, a determined result of having cancer is outputted.

In an embodiment, the following step can be performed after step S1 and before step S2, or after step S2 and before step S3: the image preprocessing module 14 processes the image (or patient image) by resampling, windowing and normalization.

The efficacy of the medical image analyzing system and method according to the present disclosure is verified as follows: first, 718 pancreatic cancer patients and 698 computer tomography images of healthy pancreases are provided; one first model and five second models are generated by training; the second models achieve a sensitivity of 89.9% (95% confidence interval, 82.7%-94.9%) and a specificity of 95.9% (95% confidence interval, 91.3%-98.5%), an area under the curve (AUC) is 0.964 (95% confidence interval, 0.942-0.986); and when the tumor size is less than 2 cm, the second models achieve a sensitivity of 87.5% (95% confidence interval, 67.6%-97.3%).

In conclusion, the medical image analyzing system and method according to the present disclosure have higher sensitivity than radiologists in identifying pancreatic cancer, which means that the medical image analyzing system and method according to the present disclosure can effectively assist radiologists in reducing their clinical missed diagnosis rate, especially in the case of tumors less than 2 cm in size. Therefore, the situation that about 40% of the tumors cannot be detected when the tumor is less than 2 cm in size in the general clinical situation can be effectively improved. In addition, the medical image analyzing system and method according to the present disclosure are automated processes. After directly inputting the original medical image, the medical image analyzing system and method according to the present disclosure can automatically identify the possible positions and ranges of pancreas and tumor and automatically classify whether the original medical image contains pancreatic cancer, so that the present disclosure can be easy to use.

The above-described descriptions of the detailed embodiments are to illustrate the implementation according to the present disclosure, and it is not to limit the scope of the present disclosure. Accordingly, all modifications and variations completed by those with ordinary skill in the art should fall within the scope of present disclosure defined by the appended claims.

What is claimed is:

1. A medical image analyzing system, comprising:
    a first neural network module having a first model and configured to input at least one patient image into the first model to obtain a result having determined positions and ranges of an organ and a tumor of the patient image;
    a second neural network module having a plurality of second models and configured to respectively input the result having the determined positions and ranges of the organ and the tumor of the patient image into the plurality of second models to obtain a plurality of prediction values corresponding to each of the plurality of second models and a model number predicting having cancer in the plurality of prediction values;
    a determining module configured to output a determined result based on the model number predicting having cancer and a number threshold value; and
    a threshold-value selection module configured to plot a plurality of curves for the plurality of prediction values, wherein a plurality of threshold values for determining whether there is cancer are determined from each of the plurality of curves, such that the second neural network module determines whether the plurality of prediction values predict having cancer based on the plurality of threshold values.

2. The medical image analyzing system of claim 1, further comprising a database stored with a plurality of images, organ position and range markers and tumor position and range markers, wherein the plurality of images, the organ position and range markers and the tumor position and range markers are interlinked to use as a first training set.

3. The medical image analyzing system of claim 2, wherein the first neural network module is trained to obtain the first model based on the first training set, wherein the first neural network module is a model searched by using a coarse-to-fine neural structure search (C2FNAS), and wherein the first neural network module uses an Adam optimizer and a cosine annealing learning rate scheduler to adjust a learning rate in a range of $10^{-4}$ to $10^{-5}$, and a loss function is set to a Dice loss combined with a categorical cross-entropy loss.

4. The medical image analyzing system of claim 3, wherein the first neural network module obtains a result having determined positions and ranges of an organ and a tumor of the plurality of images by inputting the plurality of images into the first model and uses the result as a second training set.

5. The medical image analyzing system of claim 4, wherein the second neural network module is trained to obtain the plurality of second models based on the second training set, wherein the second neural network module is a DenseNet-121, and wherein the second neural network module uses an Adam optimizer and a cosine annealing learning rate scheduler to adjust a learning rate in a range of $10^{-4}$ to $10^{-5}$, and a loss function is set to a binary classification loss.

6. The medical image analyzing system of claim 5, wherein the second neural network module evenly divides the plurality of images and the second training set into a plurality of folds, and repeatedly uses one of the plurality of folds as a validation set and the others of the plurality of folds as a training set in a non-repetitive manner to train and obtain the plurality of second models.

7. The medical image analyzing system of claim 1, wherein the plurality of curves are receiver operating characteristic curves, and wherein the plurality of threshold values are corresponding threshold values corresponding to maximum values of a plurality of Youden indexes or a combination of a sensitivity and a specificity.

8. The medical image analyzing system of claim 7, wherein the plurality of Youden indexes are calculated from the sensitivity and the specificity corresponding to each point in each of the plurality of curves according to a formula Youden index=Sensitivity+Specificity−1, wherein the combination of the sensitivity and the specificity are calculated from the sensitivity and the specificity corresponding to the each point in each of the plurality of curves according to a formula Combination of Sensitivity and Specificity=Sensitivity×N+Specificity, and wherein the N is any number.

9. The medical image analyzing system of claim 1, wherein the determining module respectively calculates corresponding positive likelihood ratios for performance of different model numbers predicting having cancer in the plurality of second models to determine the number threshold value, and wherein the determining module outputs the determined result of having cancer when the model number predicting having cancer is greater than or equal to the number threshold value.

10. The medical image analyzing system of claim 9, wherein the determining module selects a least number in the different model numbers predicting having cancer corresponding to the positive likelihood ratio greater than 1 as the number threshold value.

11. The medical image analyzing system of claim 1, further comprising an image preprocessing module configured to process the patient image by resampling, windowing and normalization before inputting the first model or the plurality of second models.

12. A medical image analyzing method, comprising:
    obtaining at least one patient image;
    inputting the patient image into a first model of a first neural network module to obtain a result having determined positions and ranges of an organ and a tumor of the patient image;
    inputting the result having the determined positions and ranges of the organ and the tumor of the patient image into the plurality of second models of a second neural network module, respectively, to obtain a plurality of prediction values corresponding to each of the plurality of second models;
    plotting a plurality of curves for the plurality of prediction values by a threshold-value selection module, wherein a plurality of threshold values for determining whether there is cancer are determined from each of the plurality of curves, such that the second neural network module determines whether the plurality of prediction values predict having cancer based on the plurality of threshold values, and obtains a model number predicting having cancer in the plurality of prediction values; and outputting a determined result by a determining module according to the model number predicting having cancer and a number threshold value.

13. The medical image analyzing method of claim 12, further comprising interlinking a plurality of images, organ position and range markers and tumor position and range markers to use as a first training set via a database stored with the plurality of images, the organ position and range markers and the tumor position and range markers.

14. The medical image analyzing method of claim 13, wherein the first neural network module is trained to obtain the first model based on the first training set, wherein the first neural network module is a model searched by using a coarse-to-fine neural structure search (C2FNAS), and wherein the first neural network module uses an Adam optimizer and a cosine annealing learning rate scheduler to adjust a learning rate in a range of $10^{-4}$ to $10^{-5}$, and a loss function is set to a Dice loss combined with a categorical cross-entropy loss.

15. The medical image analyzing method of claim 14, wherein the first neural network module obtains a result having determined positions and ranges of an organ and a tumor of the plurality of images by inputting the plurality of images into the first model and uses the result as a second training set.

16. The medical image analyzing method of claim 15, wherein the second neural network module is trained to obtain the plurality of second models based on the second training set, wherein the second neural network module is a DenseNet-121, and wherein the second neural network module uses an Adam optimizer and a cosine annealing learning rate scheduler to adjust a learning rate in a range of $10^{-4}$ to $10^{-5}$, and a loss function is set to a binary classification loss.

17. The medical image analyzing method of claim 16, wherein the second neural network module evenly divides the plurality of images and the second training set into a plurality of folds, and repeatedly uses one of the plurality of folds as a validation set and the others of the plurality of folds as a training set in a non-repetitive manner to train and obtain the plurality of second models.

18. The medical image analyzing method of claim 12, wherein the plurality of curves are receiver operating characteristic curves, and wherein the plurality of threshold values are corresponding threshold values corresponding to maximum values of a plurality of Youden indexes or a combination of a sensitivity and a specificity.

19. The medical image analyzing method of claim 18, wherein the plurality of Youden indexes are calculated from the sensitivity and the specificity corresponding to each point in each of the plurality of curves according to a formula Youden index=Sensitivity+Specificity−1, wherein the combination of the sensitivity and the specificity are calculated from the sensitivity and the specificity corresponding to the each point in each of the plurality of curves according to a formula Combination of Sensitivity and Specificity=Sensitivity×N+Specificity, and wherein the N is any number.

20. The medical image analyzing method of claim 12, wherein the determining module respectively calculates corresponding positive likelihood ratios for performance of different model numbers predicting having cancer in the plurality of second models to determine the number threshold value, and wherein the determining module outputs the determined result of having cancer when the model number predicting having cancer is greater than or equal to the number threshold value.

21. The medical image analyzing method of claim 20, wherein the determining module selects a least number in the different model numbers predicting having cancer corresponding to the positive likelihood ratio greater than 1 as the number threshold value.

22. The medical image analyzing method of claim 12, further comprising enabling an image preprocessing module to process the patient image by resampling, windowing and normalization before inputting the first model or the plurality of the second models.

* * * * *